United States Patent
Jessberger et al.

(10) Patent No.: US 9,846,165 B2
(45) Date of Patent: Dec. 19, 2017

(54) METHOD FOR INHIBITING THE SWAP-70 PROTEIN

(71) Applicant: THORNE LIMITED, Vancouver (CA)

(72) Inventors: Rolf Jessberger, Dresden (DE); Carlos Andres Chacon-Martinez, Dresden (DE)

(73) Assignee: THORNE LIMITED, Vancouver (CA)

( * ) Notice: Subject to any disclaimer, the term of this patent is extended or adjusted under 35 U.S.C. 154(b) by 0 days.

(21) Appl. No.: 14/767,210

(22) PCT Filed: Feb. 7, 2014

(86) PCT No.: PCT/EP2014/052392
§ 371 (c)(1),
(2) Date: Aug. 11, 2015

(87) PCT Pub. No.: WO2014/122245
PCT Pub. Date: Aug. 14, 2014

(65) Prior Publication Data
US 2016/0003846 A1 Jan. 7, 2016

(30) Foreign Application Priority Data
Feb. 11, 2013 (DE) .......................... 10 2013 202 206

(51) Int. Cl.
| | |
|---|---|
| *G01N 33/53* | (2006.01) |
| *A61K 38/16* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 49/00* | (2006.01) |
| *G01N 33/68* | (2006.01) |
| *G01N 33/566* | (2006.01) |
| *C07K 14/47* | (2006.01) |

(52) U.S. Cl.
CPC ......... *G01N 33/6872* (2013.01); *A61K 38/16* (2013.01); *C07K 14/47* (2013.01); *G01N 33/566* (2013.01); *G01N 2333/4703* (2013.01); *G01N 2458/30* (2013.01); *G01N 2500/00* (2013.01); *G01N 2500/04* (2013.01); *G01N 2500/10* (2013.01); *G01N 2500/20* (2013.01)

(58) Field of Classification Search
None
See application file for complete search history.

(56) References Cited

U.S. PATENT DOCUMENTS

| 6,528,284 B1 | 3/2003 | Wabl et al. |
| 2002/0072076 A1 | 6/2002 | Sakamoto et al. |
| 2009/0069420 A1 | 3/2009 | Turkson et al. |

FOREIGN PATENT DOCUMENTS

| DE | 60023261 T2 | 7/2006 |
| WO | 03/074652 A2 | 9/2003 |

OTHER PUBLICATIONS

NCBI Database, GenBank Accession No. AF053974, 2 pages (1998).*
Chacon-Martinez et al., J. Biol. Chem. 288:28687-28703 (Oct. 2013).*
International Search Report issued in PCT/EP2014/052392, dated Apr. 3, 2014.
Weidemann, et al., "Analysis of Ligand Binding by Two-Colour Fluorescence Cross-Correlation Spectroscopy," Single Molecules, vol. 3, No. 1, pp. 49-61, Mar. 11, 2002.

* cited by examiner

*Primary Examiner* — Hasan Ahmed
*Assistant Examiner* — Thea D'Ambrosio
(74) *Attorney, Agent, or Firm* — Heslin Rothenberg Farley and Mesiti, PC

(57) ABSTRACT

The invention relates to the field of biomedical and pharmacological research, in particular in the field of immunology, allergies, cancers, bone diseases and autoimmune diseases.
The invention is based on the recent finding that SWAP-70 dimerizes, that the dimerization takes place via a specific, largely unique and limited region of the protein, and that this dimerization is central to the function of the protein (and probably the stability thereof).
The invention provides a screening method which makes it possible to identify new active ingredients which, by accumulating at the dimerization domain and inhibiting SWAP-70 activity, suppress the supporting function of SWAP-70 in tumorigenesis, tumor cell migration and invasion, bone-degrading osteoclast activity, and the allergic reaction, as well as in autoimmune diseases.
The object is achieved by a method for identifying a substance which inhibits the activity of SWAP-70, wherein the method comprises the following: contacting at least one test substance with SWAP-70, detecting the degree of dimerization of SWAP-70, selecting a test substance which inhibits the dimerization of SWAP-70.

3 Claims, 3 Drawing Sheets

SEQUENCE LISTING

<160> NUMBER OF SEQ ID NOS: 1

<210> SEQ ID NO 1
<211> LENGTH: 85
<212> TYPE: PRT
<213> ORGANISM: Homo sapiens

<400> SEQUENCE: 1

```
Gln Asp Glu Glu Thr Val Arg Lys Leu Gln Ala Arg Leu Leu Glu Glu
1               5                   10                  15

Glu Ser Ser Lys Arg Ala Glu Leu Glu Lys Trp His Leu Glu Gln Gln
            20                  25                  30

Gln Ala Ile Gln Thr Thr Glu Ala Glu Lys Gln Glu Leu Glu Gln Gln
        35                  40                  45

Arg Val Met Lys Glu Gln Ala Leu Gln Glu Ala Met Ala Gln Leu Glu
    50                  55                  60

Gln Leu Glu Leu Glu Arg Lys Gln Ala Leu Glu Gln Tyr Glu Gly Val
65                  70                  75                  80

Lys Lys Lys Leu Glu
                85
```

METHOD FOR INHIBITING THE SWAP-70 PROTEIN

CROSS REFERENCE TO RELATED APPLICATIONS

This application is a U.S. National Phase filing under 35 U.S.C. §371 of International Application No. PCT/EP2014/052392, filed Feb. 7, 2014, and published as WO 2014/122245-A1 on Aug. 14, 2014, which claims benefit of priority from German Patent Application Serial No. DE 10 2013 202 206.9, filed Feb. 11, 2013. The entire contents of each of the prior applications are incorporated herein by reference in their entirety.

The invention relates to the field of biomedical and pharmacological research, in particular in the field of immunology, allergies, cancers, bone diseases and autoimmune diseases.

PRIOR ART

Cancers, allergies, including asthma, autoimmune diseases and osteoporosis are very widespread diseases worldwide, some of which are increasing; in severe cases, cancer, autoimmune diseases and allergies can result in death.

The incidence of allergies has tripled in the last 20 years. Between 5 and 10% of the world's population suffers from allergies, including asthma, of which about one fifth of those people suffer. Asthma is the most common chronic disease in the under 18 s. Allergies are triggered by excessive IgE production by the B-lymphocytes. Interventions in the regulation of this IgE production are thus in principle groundbreaking for a causal therapy for allergies, which has hitherto not existed. However, too little is as yet known about how IgE production is regulated specifically.

As has been known for a relatively long time, IgE production depends on the function of the STAT-6 protein, which activates transcription. It is also known that the effect of STAT-6 on IgE production is inhibited by BCL-6. BCL-6 and STAT-6 bind an overlapping region of the regulatory DNA sequence of the IgE gene. It is assumed that BCL-6 interacts with co-repressors and thereby actively inhibits IgE production. This repression is specific for the IgE gene, since BCL-6 selectively binds to the STAT-6 binding site in the IgE gene and does not bind to most other STAT-6 binding sites. However, the exact mechanisms of the specificity and regulation of the critical balance between BCL-6 and STAT-6 are not known.

The SWAP-70 protein is expressed mainly in activated B-cells, in mast cells, in osteoclasts and in dendritic cells, although the presence of the protein in the cytoplasm of other cell types cannot be excluded (Borggrefe et al. 1998; Borggrefe et al. 1999; Masat et al. 2000; Gross et al. 2002; Pearce et al. 2006; Ocana-Morgner et al. 2009). SWAP-70 is expressed in particular in cell transformation, that is to say the formation of tumour cells from primary cells, and in tumour cell lines of various origins. It is known that SWAP-70-deficient mice exhibit specific changes of the phenotype, inter alia the CD40-mediated activation of B-cells, including the change to the production of IgE, and the degranulation of mast cells are greatly reduced (Borggrefe et al. 2001; Gross et al. 2002). With regard to IgE production in dependence on SWAP-70, it has been shown that, in SWAP-70-deficient mice, greatly reduced IgE concentrations are present before and after immunisation, and that the production of secreted IgEs in B-cell cultures is reduced about 8-fold. However, the production of other immunoglobulin classes is not substantially impaired.

U.S. Pat. No. 6,528,284 B1 (US 2003/143611 A1, WO 99/03991 A1) discusses the purification and characterisation of proteins which are involved generally in immunoglobulin class switching. SWAP-70 was identified, which is here referred to and claimed as SRTA-70 (S-region transfer activity-70). Its general role in immunoglobulin class switching is described, as well as the use of that protein in modulating class switching.

US 2003/0166018 A1 describes the role of SWAP-70 in mast cell degranulation and claims a method for identifying an agent which reduces the content of SWAP-70 protein in a mast cell.

WO 2011/141267 A1 discloses a screening method for identifying active ingredients which inhibit IgE production. The basis of this method is the regulatory action of SWAP-70 on STAT-6 and BCL-6, which in turn influence IgE production.

Allergies are nowadays treated predominantly by treating the symptoms, that is to say by alleviating the allergic reaction by means of antihistamines or glucocorticoids, for example, but not by causal therapy. Disadvantages of current therapies are inter alia a short action, lack of treatment of the underlying cause, non-specific action and side-effects.

The only IgE inhibitor known to date is omalizumab, a recombinant humanised monoclonal anti-immunoglobulin E (anti-IgE) antibody for treating severe allergic asthma. However, even omalizumab does not causally suppress IgE production but instead traps IgE that has already been produced, resulting in the formation of immunoglobulin complexes. It is a disadvantage that antibody therapies can themselves trigger allergic reactions or immune reactions that attack the antibody protein. In addition, antibodies are pharmacologically expensive to produce.

SWAP-70 further plays an important role in cancers. It has been shown that overexpression of SWAP-70 can transform human cells into tumour cells. Furthermore, it has been shown that SWAP-70 assists the cell migration of tumour cells, that is to say promotes their invasivity, which is important in the formation of metastases in particular. SWAP-70 occurs in overexpressed and/or mutated form in various tumour cells or human tumours. For example, primary mouse embryonic fibroblasts are transformed into tumour cells by expression of a mutated SWAP-70 gene.

In addition, it has been possible to demonstrate that the activity of osteoclasts, that is to say cells that degrade bone substance, is inhibited by eliminating SWAP-70. SWAP-70 assists osteoclast activity by promoting the migration and cytoskeletal dynamics of these cells. In osteoporosis, osteoclasts are hyperactive. Inhibiting SWAP-70 will therefore inhibit bone degradation in osteoporosis.

Allergies are treated predominantly by treating the symptoms, that is to say alleviating the allergic region, for example by means of antihistamines with known side-effects, but not by causal therapy. Blocking IgE production in B cells and/or mast cell degranulation represent causal therapeutic approaches, which can also complement each other. Cancer therapy requires a large number of complementary approaches. Therapeutic success, both in the case of primary tumours and in the case of metastases, continues to be very unsatisfactory. New approaches, new target molecules, are therefore essential. Osteoporosis, which, like the diseases mentioned above, is a very widespread disease, is predominantly treated either by means of bisphosphonates, which have been in use for a relatively long time, or, more recently (experimentally), by means of osteoclast growth factor inhibitors. Both approaches have considerable disadvantages. Bisphosphonates inhibit RhoGTPases in almost all cells and are therefore associated with significant side-effects when used for prolonged periods. Growth factor inhibitors are often difficult to produce and/or very expensive (antibodies, cytokines) and/or act upon other cells or systems (inflammation).

SWAP-70 also plays a central role in autoimmune diseases, including multiple sclerosis. There is as yet no therapeutic curative treatment for multiple sclerosis.

OBJECT OF THE INVENTION

The object of the invention is, therefore, to provide a method by means of which it is possible purposively to seek active ingredients which can be used as novel antiallergics as well as for the treatment of osteoporosis, multiple sclerosis and cancer, and which in particular inhibit the production of IgE. The invention is further to provide means for carrying out the screening method.

DESCRIPTION OF THE INVENTION

The invention is based on the recent finding that SWAP-70 dimerises, that the dimerisation takes place via a specific, largely unique and limited region of the protein, and that this dimerisation is central to the function of the protein (and probably the stability thereof). The dimerisation domain has been identified as a particularly acidic region and has an extremely high Q/E content of about 41%. It has been possible to show that dimerisation is required for the functional F-actin interaction of SWAP-70, which underlies the function of SWAP-70. Mutants in which the corresponding dimerisation domain is missing do not dimerise and do not bundle F-actin filaments. It has further been possible to show that functional osteoclasts require the dimerisation domain of SWAP-70.

Substances which accumulate at the dimerisation domain of SWAP-70 and thus prevent the dimerisation of SWAP-70 and thereby inhibit the activity of SWAP-70 are accordingly suitable as novel antiallergics, as well as for the treatment of osteoporosis and cancer.

On the basis of these findings, the invention provides a screening method which makes it possible to identify novel active ingredients which, by accumulating at the dimerisation domain and inhibiting SWAP-70 activity, suppress the supporting function of SWAP-70 in tumourigenesis, tumour cell migration and invasion, bone-degrading osteoclast activity, and the allergic reaction.

SWAP-70 is a unique protein in terms of domain structure and sequence arrangement, and it has only a single related protein in the entire genome. However, that other protein does not carry the dimerisation sequence typical of SWAP-70. An inhibitor of the dimerisation of SWAP-70 will therefore have no or little effect on other proteins and will be correspondingly specific.

On account of its uniqueness, SWAP-70 represents an ideal additional starting point in multifactor combination therapy as is indispensable, for example, in the case of cancer. By inhibiting SWAP-70, an important additional pathway or process is inhibited. Combination therapy is likewise suitable in the case of allergies, autoimmune diseases, in particular multiple sclerosis, and osteoporosis.

SWAP-70 is involved mostly in causal processes of the above-mentioned diseases. Inhibition of SWAP-70 would therefore be a causal therapy instead of merely alleviating symptoms.

In particular in IgE production in B-cells, SWAP-70 acts in a unique manner in the cell nucleus of the cells, that is to say a particularly high specificity is ensured.

The object is achieved by a method for identifying a substance which inhibits the activity of SWAP-70, wherein the method comprises the following:
(i) contacting:
  (a) at least one test substance with
  (b) SWAP-70,
(ii) detecting the degree of dimerisation of SWAP-70,
(iii) selecting a test substance which inhibits the dimerisation of SWAP-70.

The degree of dimerisation of SWAP-70 can be detected by a very wide variety of known methods. The degree of dimerisation is understood as being the proportion of the molecules that are present in the form of dimers.

In the screening method according to the invention, test substances are to that end preferably brought into contact with SWAP-70 monomers. Because dimerisation is a reversible equilibrium reaction, this does not rule out the possibility of some of the SWAP molecules being present in the form of dimers.

The dimerisation of SWAP-70 can be inhibited in two ways: immediately after translation, that is to say before dimerisation, or as the inhibition of the re-dimerisation of monomers. After the dissociation of dimers, an inhibitor is able to bind the resulting monomers and prevent re-dimerisation. If the inhibitor has a very high affinity which is higher than the affinity between monomers, it will suppress the dimerisation from the outset but also effectively cleave dimers by preventing re-dimerisation. The equilibrium of the reaction is shifted in favour of the monomers.

For detecting the degree of dimerisation, two differently labelled SWAP-70 molecules are preferably used. Labelling is preferably by means of fluorescent markers or affinity tags. Alternatively, only one of the SWAP-70 molecules is labelled and the other is fixed to a carrier or a surface. Alternatively, the dimerisation is measured on the basis of the change caused by dimerisation in the diffusion in solution of a labelled SWAP-70 molecule or of two different SWAP-70 molecules, or by fluorescence cross correlation spectroscopy (FCCS).

The two SWAP-70 molecules are generally identical in terms of their sequence and structure and differ only by their respective binding to one or more markers or to a carrier or a surface.

The test substances are preferably so-called small molecules, that is to say compounds having a molecular weight up to 800 daltons (atomic mass unit u). The test substances are preferably organic molecules or also peptides.

In the method according to the invention, it is possible to carry out in parallel both a test with single test substances and a screening for a plurality of test substances.

The degree of dimerisation of SWAP-70, or the interaction of the SWAP-70 monomers with the test substances, is preferably measured in vitro or in situ.

In vitro (that is to say in cell-free methods), the action of the test substance(s) on the SWAP-70 dimerisation, or the interaction between the SWAP-70 molecules (together also referred to hereinbelow as binding partners), is preferably tested using the corresponding purified proteins as binding partners. This takes place, for example, in binding assays, in which the association of a labelled binding partner with an unlabelled binding partner or of two differently labelled binding partners is measured. Tests of this type can be performed inter alia by the multiwell method (similarly to an ELISA) or in solution (for example by means of Alpha- Screen) by the high throughput method. Markers can be, for example, fluorescent dyes which are bound covalently to one binding partner or to both binding partners. Alternatively, the labelling is carried out radioactively, by means of affinity tags, haptamers or by labelling with fluorescent proteins (preferably as fusion protein—for example with GFP). The retention of the fluorescence signals on the unlabelled partner or the fluorescence interference between associated partners is read out.

In situ (that is to say in cells, preferably in cell culture), the action of the test substance(s) on SWAP-70 dimerisation is preferably measured in cells which express SWAP-70. The interaction between the binding partners is here preferably likewise detected by FRET or also in cell lysates. Here too, the individual binding partners (SWAP-70 molecules) are labelled, for example, by means of affinity tags (for example His-tag) and corresponding affinity binding materials (such as, for example, $Ni^{2+}$) are bound to those materials.

The action of cell-penetrating test substances influences the binding partners in a manner similar to that described above for the in vitro methods. The in situ methods are preferably carried out by means of conventional cell lines which can easily be cultivated and transfected and in which the binding partners are expressed. Suitable cell lines are, for example, NIH3T3, 293T and COS-7. Interactions between the binding partners can advantageously also be analysed in non-mammalian cell systems, for example in yeast cells (yeast 2-hybrid system) or insect cells (co-precipitation after expression) or after co-translation in cell-free systems (in vitro transcription/translation systems, followed by co-precipitations, so-called pull-downs). As negative controls there are preferably used corresponding cells or cell lines in which the genes that code for any individual proteins are not present or have been deleted (for example cells from SWAP-70-/- mice, such as, for example, mouse embryonic fibroblasts). Multiwell formats permit high throughput screening methods. The term cells preferably does not include human embryonic stem cells which have been obtained by destroying human embryos.

The interaction of the binding partners is preferably detected in vitro or also in the cell by Förster resonance energy transfer (FRET) analyses. To that end, the SWAP-70 molecules are preferably labelled with two molecules which are different from one another and are suitable for producing a FRET. These two different molecules are also referred to hereinbelow as FRET donor and FRET acceptor (or simply donor and acceptor).

The Förster resonance energy transfer (FRET) is a physical process in which energy of an excited donor can be transferred non-radiatively to an acceptor at a distance of approximately from 1.5 to 10 nm. The molecules are so selected that the emission spectrum of the donor molecule overlaps with the excitation spectrum of the acceptor. If both the donor and the acceptor are fluorescent dyes, the expression fluorescence resonance energy transfer is used. If, on the other hand, the donor or acceptor is a chemiluminescence or bioluminescence source, the expression chemiluminescence resonance energy transfer (CRET) or bioluminescence resonance energy transfer (BRET) is used.

For in vitro assays, the donor and/or the acceptor is preferably bound to the binding partner covalently or by coordination. The protein is preferably labelled covalently at free amino groups or carboxyl groups of the amino acid side chains (lysine or aspartate or glutamate residues) of the protein. Organic or inorganic fluorescent dyes are preferably used as donors and acceptors in the invention. Preferably from 1 to 40, particularly preferably from 1 to 5, dye molecules are bound per protein molecule. As inorganic fluorescent dyes there are used, for example, europium (preferably $Eu^{3+}$), cerium or terbium or so-called quantum dots, such as, for example, doped $LaF_3$ and $LaPO_4$ nanoparticles.

The binding of a biomolecule, such as fluorescent proteins (for example GFP, YFP and CFP) and/or luciferase, is carried out either by crosslinking or by producing a fusion protein. Fusion proteins with such biomolecules advantageously also allow the interaction of the binding partners to be detected in situ (in the cell). Luminescence sources (such as luciferase) and fluorescent proteins can advantageously be used as acceptors and donors.

Alternatively to cells, multicellular organisms can also be used for the method. In that case, the interaction of the binding partners is preferably determined in vivo. Other multicellular organisms are selected from vertebrates (excluding humans) and invertebrates, such as *Drosophila melanogaster, Caenorhabditis elegans, Xenopus laevis, Oryzias latipes, Danio rerio* or *Mus musculus*, or embryos thereof.

Preferred donor-acceptor pairs and their respective excitation maxima ($Max_{ex}$) and emission maxima ($Max_{em}$) are selected from:

| Donor | | | Acceptor | | |
| --- | --- | --- | --- | --- | --- |
| Name | $Max_{ex}$ | $Max_{em}$ | Name | $Max_{ex}$ | $Max_{em}$ |
| Alexa Fluor 488 | 495 nm | 519 nm | Alexa Fluor 555 (or Alexa Fluor 546 or 568) | 555 nm | 565 nm |
| Alexa Fluor 546 | 556 nm | 573 nm | Alexa Fluor 633 | 632 nm | 647 nm |
| Alexa Fluor 555 | 555 nm | 565 nm | Alexa Fluor 647 | 650 nm | 668 nm |
| Alexa Fluor 568 | 578 nm | 603 nm | Cy5 | 649 nm | 670 nm |
| Alexa Fluor 568 (or Cy3) | 578 nm | 603 nm | Alexa Fluor 633 (or Cy5 or Alexa Fluor 647) | 632 nm | 647 nm |
| Europium ($Eu^{3+}$) | 395 nm 466 nm | 617 nm | Allophycocyanin | 650 nm | 660 nm |
| $Eu^{3+}$ (or $LaF_3$) | 395 nm | 591 nm | Alexa Fluor 594 (or Alexa Fluor 610 or 633) | 590 nm | 630 nm |
| $LaPO_4$ (or Ce or Tb) | 266 nm | 542 nm | Alexa Fluor 532 | 530 nm | 560 nm |
| Cyan fluorescent protein (CFP) | 452 nm | 505 nm | Yellow fluorescent protein (YFP) | 514 nm | 527 nm |

-continued

| | Donor | | | Acceptor | |
|---|---|---|---|---|---|
| Name | $\text{Max}_{ex}$ | $\text{Max}_{em}$ | Name | $\text{Max}_{ex}$ | $\text{Max}_{em}$ |
| Luciferase | | | YFP | 514 nm | 527 nm |
| EGFP | 488 nm | 509 nm | YFP | 514 nm | 527 nm |

FRET analyses are also suitable for high throughput screening. A FRET donor is bound to one binding partner and a FRET acceptor is bound to the other, the two together forming a FRET pair. If the two binding partners are present independently of one another in vitro or in the cell, no FRET occurs. By the interaction of the two binding partners, the FRET donor and the FRET acceptor are brought into direct proximity, as a result of which the FRET is initiated.

As a result of the FRET, the radiation emission and the fluorescence lifetime of the donor decrease, and the acceptor emission increases. This results in a measurable shift of the wavelength of the emitted light upon interaction of the binding partners, which is detected by means of suitable instrumental methods. There are suitable for this purpose, for example, a fluorescence microscope, flow cytometer, fluorimeter or plate spectrophotometer.

The test substances influence the interaction of the binding partners. Test substances which inhibit the dimerisation of SWAP-70 or reduce the interaction of SWAP-70 monomers with one another are selected.

The degree of dimerisation of SWAP-70 can likewise be detected according to the invention indirectly by detecting the molecule size by means of chromatography. To that end, on the one hand SWAP-70 molecules and on the other hand SWAP-70 molecules mixed with a test substance are applied to the mobile phase. SWAP-70 dimers can be distinguished by different migration distances of SWAP-70 monomers. Conclusions can thereby be drawn regarding the influence of the test substance on the dimerisation.

The degree of dimerisation of SWAP-70 can further be detected by means of a quartz microbalance. To that end, SWAP-70 molecules are fixed to an oscillating crystal. The frequency changes upon addition of further SWAP-70 molecules in combination with a test substance are compared with the frequency changes upon addition of further SWAP-70 molecules without test substance. This comparison allows conclusions to be drawn regarding the degree of dimerisation with and without addition of the test substance, and thus regarding the action of the test substance.

The degree of dimerisation of SWAP-70 can further be detected according to the invention by means of surface plasmon resonance. SWAP-70 molecules are thereby bound to a surface. The change in the light refraction upon addition of further SWAP-70 molecules is measured. This change in the light refraction is compared with the change in the light refraction that results from the addition of further SWAP-70 molecules in combination with a test substance.

When a method selected from surface plasmon resonance, chromatography or measurement of the frequency change by means of a quartz microbalance is used, the SWAP-70 molecules do not necessarily have to differ by their binding to one or more markers or to a carrier or a surface.

The test substances determined by the method according to the invention are preferably tested further for biological effectiveness, in particular inhibition of IgE production, mast cell degranulation, bone-resorbing osteoclast activity, cell transformation of primary cells into tumour cells, the migratory behaviour of tumour cells. To that end, B-lymphocytes are preferably excited to IgE production in situ or in vivo. Isolated spleen cells (for example from the mouse) are preferably used because they contain a large number (>60%) of B-lymphocytes. The B-lymphocytes can be, but do not have to be, purified. The B-lymphocytes can be excited to IgE production by means of IL-4 (preferably murine and, for example, recombinantly produced) and CD40L (for example by fixed CD40L-expressing cells). The IgE production can be measured simply and with a high throughput, for example by means of FACS analysis or ELISA. Test substances which reduce IgE production are preferably selected.

The substances identified by the method according to the invention are suitable in particular for the treatment of IgE-mediated allergies, in particular for the treatment of IgE-dependent allergic reactions, or type I allergies, and of IgE-dependent autoimmune diseases. The substances identified in the method according to the invention are suitable in particular for the treatment of IgE-dependent diseases such as allergic asthma, allergic rhinitis, allergic conjunctivitis, allergic reactions of the gastrointestinal tract (in particular vomiting and diarrhoea), neurodermatitis, psoriasis, contact eczema, urticaria, allergic oedemas, in particular laryngeal oedema and angioedema (Quincke's oedema), anaphylactic shock, allergic vasculitis, angiitis or granulomatosis (Churg-Strauss syndrome), hyper-IgE syndrome, Omenn syndrome, some forms of 22q11 syndrome, rheumatoid arthritis, lupus erythematosus, type I diabetes, Sjogren's syndrome and bullous pemphigoid.

The substances identified by the method according to the invention are further suitable for the treatment of autoimmune diseases such as, for example, multiple sclerosis.

The substances identified by the method according to the invention are further suitable for the treatment of osteoporosis by inhibiting the SWAP-70-dependent bone-resorbing activity of the osteoclasts, as well as for the treatment of cancer, in particular, but not limited to, lymphoma, leukaemias, glioblastoma, cancer stem cells, breast carcinomas, sarcoma.

The invention also provides the dimerisation domain of SWAP-70, comprising the following sequence:

(SEQ ID No. 1)
QDEETVRKLQARLLEEESSKRAELEKWHLEQQQAIQTTEAEKQELEQ

QRVMKEQALQEAMAQLEQLELERKQALEQYEGVKKKLE or a sequence with 70%, preferably 80%, sequence identity with SEQ ID No. 1 or a partial sequence having at least 50, preferably at least 70, more preferably at least 80, amino acid residues. The dimerisation domain of SWAP-70 has a length of up to 100 amino acid residues.

The dimerisation domain of SWAP-70 is distinguished by a high content of acidic amino acid residues. Preferably from 15% to 25%, especially from 20% to 25%, of the amino acid residues are selected from aspartic acid (Asp/D) and glutamic acid (Glu/E), particularly preferably from 20% to 25% of the amino acid residues are glutamic acid (Glu/E).

The dimerisation domain of SWAP-70 additionally has a very high content of polar residues. Preferably from 50% to 70%, especially from 55% to 65%, of the amino acid residues are selected from aspartic acid (Asp/D), glutamic acid (Glu/E), glutamine (Gln/Q), lysine (Lys/K), arginine (Arg/R), serine (Ser/S) and threonine (Thr/T). Preferably from 10% to 20%, especially from 13% to 17%, of the amino acid residues are selected from lysine (Lys/K) and arginine (Arg/R).

The above-described domain is preferably used in the screening method.

The invention likewise provides a test kit for identifying substances which inhibit the activity of SWAP-70, containing two differently labelled SWAP-70 charges or surface-bound and soluble SWAP-70.

Such a test kit is preferably used to screen for substances which inhibit the dimerisation of SWAP-70 monomers.

The invention likewise provides the use of such a test kit for identifying a substance which inhibits the activity of SWAP-70.

For in vitro assays, the SWAP-70 molecules are in each case in the form of isolated proteins.

The proteins are preferably bound as described above to a carrier material (for example a multiwell plate or a membrane) or provided with a marker. Where a SWAP-70 molecule is bound to a carrier material, the dimerisation is preferably detected in a manner similar to an ELISA or an ELISPOT assay. To that end, the second SWAP-70 molecule is preferably provided with a marker (preferably an affinity tag such as biotin or a haptamer).

For in situ or in vivo assays, the SWAP-70 molecules are preferably in a cell or a multicellular organism.

The proteins are here preferably provided with a marker as described above, which marker is preferably selected from affinity tags, haptamers, fluorescent or chemiluminescent biomolecules. Labelling is here preferably effected by expression as a fusion protein (protein+marker).

Preferably, as described above, two markers are selected which are suitable for producing a Förster resonance energy transfer (FRET).

BRIEF DESCRIPTION OF THE FIGURES

The invention will be described in greater detail below by means of figures and examples, without being limited thereto.

EXAMPLE 1: PULL-DOWN ASSAY FOR DIMERISATION

A pull-down assay with purified recombinant GST-SWAP-70 and SWAP-70 demonstrated the interaction between these two proteins.

For the in vitro pull-down assay, 0.4 µM purified GST-SWAP-70 and His-SWAP-70 or GST for control were mixed in 20 mM Tris, pH 7.5, 100 mM NaCl, 10% glycerol, 1 mM EDTA, 25 mM $CaCl_2$, 0.1% NP40 and 1 mM DTT were mixed and shaken for 1 hour at 4° C. Glutathione agarose beads were then added and the samples were incubated for 30 minutes, washed and resuspended in SDS-Page loading buffer. The samples were then subjected to SDS-Page and immunoblotting.

Figure 1:
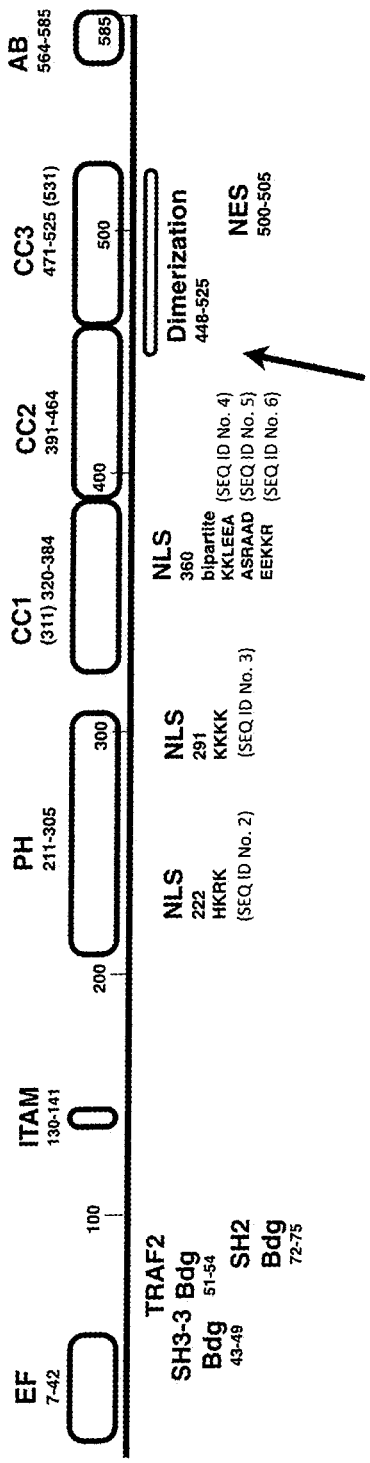
FIG. 1 shows schematically the structure of a SWAP-70 protein. The SWAP-70 protein consists of the N-terminal EF hand domain, a pleckstrin homology domain (PH) which binds $PIP_3$ and is responsible for the localisation of the membrane, a three-part coiled coil domain (CC1, CC2, CC3) and a C-terminal F-actin binding site (AB), by which SWAP-70 binds specifically to non-muscular actin (but not to muscular actin). The dimerisation domain is identified by a black bar and is located predominantly in the CC3 domain.
Figure 2:
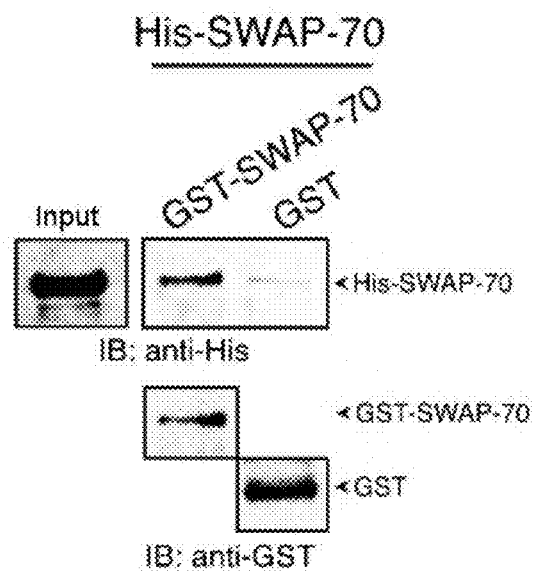
FIG. 2 shows the results of the gel electrophoresis from Example 1. It is clear that GST-SWAP-70 and His-SWAP-70 interact with one another. In the top part of the figure it can be seen that His-SWAP-70 is bound to GST-SWAP-70, visualised by addition of anti-His. If only GST is present, however, and not GST-SWAP-70, His-SWAP-70 has no binding partner, is washed out and does not provide a binding site for anti-His. Controls without His-SWAP-70 are shown in the bottom part of the figure.
Figure 3:
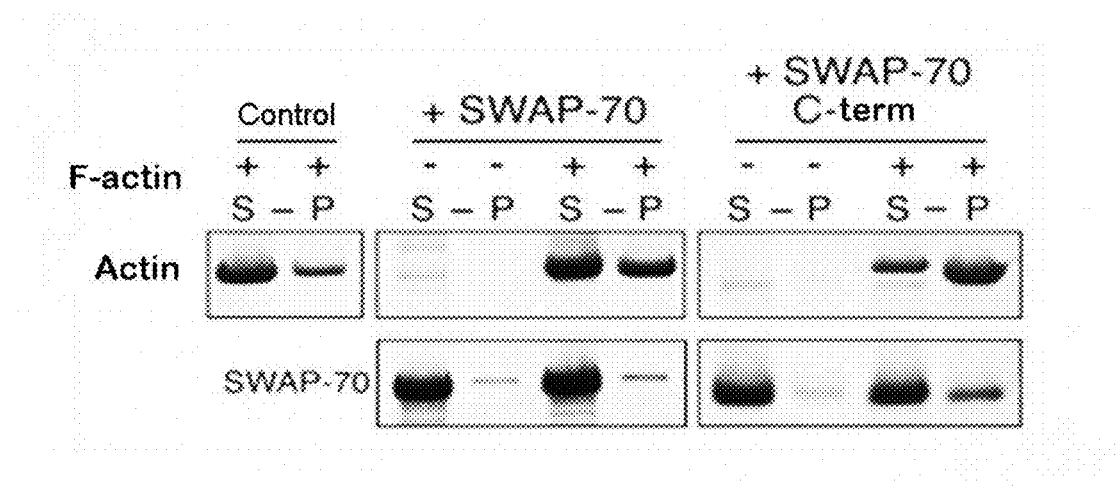
FIG. 3 shows the results of the gel electrophoresis from Example 3. S=supernatant, P=pellet.
Figure 4:
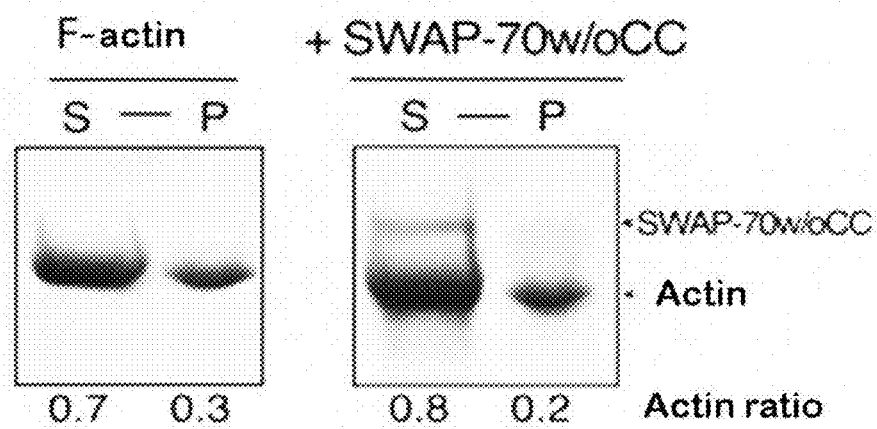
FIG. 4 shows the results of the gel electrophoresis from Example 4. S=supernatant, P=pellet.

In the gel figure (FIG. 2), it can clearly be seen that GST-SWAP-70 and His-SWAP-70 interact with one another.

EXAMPLE 2: GEL FILTRATION FOR DIMERISATION

For further testing of the oligomerisation, recombinant, purified SWAP-70, SWAP-70w/oCC (mutant in which the dimerisation domain is missing) and SWAP-70 C-term (shortened SWAP-70 with actin binding domain and a portion of the dimerisation region) as well as protein standards (gel filtration marker kit for proteins, molecular weight 29-700 kDa, Sigma) were analysed individually by means of gel filtration at a throughput of 60 ml/h on a Superdex 200 HPLC column (Amersham Pharmacia Biotech). The elution volumes of the protein standards were fitted to a curve in relation to their theoretical molecular weight. This curve was used to determine the experimental molecular weights.

The experimentally determined molecular mass of SWAP-70 was 151±17.6 kDa, approximately twice the theoretical molecular mass of SWAP-70 (71.6 kDa), which suggests that dimers have formed.

The experimentally determined molecular mass of SWAP-70 C-term was 79±3.5 kDa, which, compared with the theoretical molecular mass of 19 kDa, suggests tetramerisation.

The experimentally determined molecular mass of SWAP-70w/oCC was 50±3 kDa, which corresponds approximately to the theoretical molecular mass of 46 kDa and shows that SWAP-70 mutants in which the dimerisation domain is missing do not dimerise.

The results are listed briefly below in table form:

| Protein | Theoretical molecular mass [kDa] | Experimentally determined molecular mass [kDa] |
|---|---|---|
| SWAP-70 | 71.6 | 151 ± 17.6 |
| SWAP-70 C-term | 19 | 79 ± 3.5 |
| SWAP-70w/oCC | 46 | 50 ± 3 |

EXAMPLE 3: SWAP-70 BUNDLES ACTIN FILAMENTS BY MEANS OF ITS C-TERMINAL REGION

The actin bundling activity of SWAP-70 was tested by means of low-speed centrifugation. In the same manner, the actin bundling activity of SWAP-70 C-term was tested.

Actin (3 µM) was first polymerised. This was followed by mixing with SWAP-70, or with SWAP-70 C-term, incubation at room temperature for 30 minutes and centrifugation at 13,000 rpm and 4° C. for 30 minutes. A control was treated in the same manner without the addition of SWAP-70 or SWAP-70 C-term. The supernatants were removed and precipitated with ice-cold acetone. The pellets, which contained the crosslinked F-actin, were washed and resuspended in 1×SDS-Page loading buffer. The samples were analysed on Coomassie-stained gel. The protein bands were quantified by means of densitometry using Fiji software.

While significantly more actin was present in the supernatant than in the pellet in the control (left-hand part), this ratio was displaced in favour of the pellet by the addition of SWAP-70 and SWAP-70 C-term. Because SWAP-70 C-term is capable, because of tetramerisation, of bundling more actin filaments than SWAP-70, the corresponding band on the gel figure (on the far right) is stronger than the actin band in the pellet upon addition of SWAP-70 (middle).

EXAMPLE 4: THE DIMERISATION OF SWAP-70 BRINGS ABOUT ACTIN BUNDLING

The actin bundling activity of SWAP-70w/oCC was tested by means of low-speed centrifugation.

Actin (3 µM) was first polymerised. This was followed by mixing with SWAP-70w/oCC, incubation at room temperature for 30 minutes and centrifugation at 13,000 rpm and 4° C. for 30 minutes. A control was treated in the same manner without the addition of SWAP-70w/oCC. The supernatants were removed and precipitated with ice-cold acetone. The pellets, which contained the crosslinked F-actin, were washed and resuspended in 1×SDS-Page loading buffer. The samples were analysed on Coomassie-stained gel. The protein bands were quantified by means of densitometry using Fiji software.

An additional band was detected in the sample that contained SWAP-70w/oCC as compared with the control, which shows that SWAP-70w/oCC had not bound to actin. Because SWAP-70w/oCC lacks the dimerisation domain, this suggests that actin bundling takes place with the involvement of the dimerisation domain.

EXAMPLE 5: DETECTION OF DIMERISATION IN VIVO BY FRET

10 µg of Venus-SWAP-70 and Cerulean-SWAP-70 (Venus is an improved yellow fluorescent protein and Cerulean an improved cyan fluorescent protein) are transfected with Lipofectamin 2000 (Invitrogen) in NIH 3T3 cells which had been grown for 16 hours on coverslips coated with poly-(L-lysine) (100 µg/ml). The serum was then removed from the cells for a period of 2 hours, whereupon they are stimulated with 15 nM EGF (PeproTech) in Dulbecco's modified Eagle's medium (DMEM) and immediately fixed for 10 minutes with 4% polyformaldehyde (PFA), PBS (phosphate buffered saline). Acceptor Photobleaching FRET Makro, LAS software (Leica) is used to record images. The fluorescence intensities are detected before and after the bleaching of a region of interest with a 510 nm laser (100% power). The FRET efficiency is determined with the pbFRET v1 plugin (Mike Lorenz, MPI-CBG, Germany) using ImageJ (NIH) or Fiji. The samples are analysed at room temperature using a Leica TCS SP5 confocal laser scanning microscope (Leica, Germany) and an HCX PL APO 63X 1.4 NA by means of oil objective. The images are captured in the linear region of the reaction of the detectors, pixel saturation being prevented with LAS AF software (Leica), and analysed by Fiji.

EXAMPLE 6: DETERMINATION OF THE DIMERISATION IN VITRO BY DIFFUSION ANALYSIS AND FLUORESCENCE CROSS CORRELATION SPECTROSCOPY

In each case 1 µg of SWAP-70 protein is labelled either with the fluorescent dyes Alexa 488 or with Atto 655, approximately from 1 to 2 molecules of the dye in question being bound per molecule of SWAP-70. The SWAP-70 protein so labelled is brought in a confocal microscope in solution into a measuring chamber and excited by means of one laser (labelling with one dye) or two lasers (combination of the two differently labelled SWAP-70 molecules). The diffusion of a labelled SWAP-70 is measured over time and correlates with the monomeric, dimeric or multimeric state of the protein, which can accordingly be derived therefrom. The reciprocal influencing of the two different labellings that occurs as a result of the dimerisation is determined as fluorescence cross correlation. Both methods confirm the existence of SWAP-70 dimers. A shortened (42 kDa based on gel filtration and SDS gel electrophoresis) protein, SWAP-70w/oCC, in which the above-mentioned dimerisation sequence is missing, proved to be a monomer in these tests too.

The following tables show examples of results of mass calculations based on diffusion times. The diffusion time of a molecule is directly proportional to the spatial root of the molecular mass, which accordingly can approximately be determined according to the formula below. The molecular mass of the dyes is used for calibration.

$$\frac{\tau_d^{S70}}{\tau_d^{dye}} = \frac{\sqrt[3]{MW^{S70}}}{\sqrt[3]{MW^{dye}}}$$

The measured diffusion times of the dyes Atto 655 and Alexa 488 were used according to this formula to calculate the molecular mass of SWAP-70 or of the above-mentioned SWAP-70w/oCC fragment. Table 1 shows the diffusion times.

TABLE 1

| | Diffusion time | | | | | |
|---|---|---|---|---|---|---|
| Diffusing molecule | SWAP-70 red (Alexa) | SWAP-70 green (Atto) | Atto 655 | Alexa 488 | 42 kDa fragment red | 42 kDa fragment green |
| Diffusion time (µs) | 247 ± 5 | 207 ± 7 | 37 ± 1.4 | 33 ± 0.6 | 161 ± 3 | 130 ± 2 |

Table 2 shows the number of monomers per molecule, obtained from the molecular mass derived from the diffusion time, for either red or green dyed SWAP-70, based on the individual dyes used as standards or the SWAP-70w/oCC fragment. The results show a very good approximation to a dimeric molecular structure and thus confirm the results of the gel filtration showing the above-mentioned dimeric SWAP-70.

TABLE 2

Number of SWAP-70 monomers per SWAP-70 molecule, based on the indicated standards.

| Standard | No. of monomers SWAP-70 red | No. of monomers SWAP-70 green |
|---|---|---|
| 42 kDa fragment | 2.1 ± 0.3 | 2.6 ± 0.5 |
| Atto 655 or Alexa 488 | 2.6 ± 0.6 | 2.3 ± 0.4 |

What is claimed is:

1. A method for identifying a substance which inhibits dimerization of switch-associated protein-70 (SWAP-70), wherein the method comprises the following:
    (i) contacting:
        (a) a test substance with
        (b) a dimerization domain of SWAP-70 consisting of the sequence QDEETVRKLQARLLEEESSK-RAELEKWHLEQQQAIQTTEAEKQELE QQRVM-KEQALQEAMAQLEQLELERKQALEQYEGVK-KKLE (SEQ ID No. 1) or a partial sequence thereof having at least 70 contiguous amino acid residues of SEQ ID NO: 1;
    (ii) detecting the degree of dimerization of the SWAP-70 dimerization domain in a sample containing the SWAP-70 dimerization domain and said test substance and in a sample containing the SWAP-70 dimerization domain that does not contain test sample, and
    (iii) identifying the test substance as an inhibitor of the dimerization of SWAP-70 when dimerization in the sample containing said test substance is decreased compared to dimerization in the sample that does not contain test sample.

2. The method of claim 1, wherein a FRET-based assay is performed to detect the degree of dimerization.

3. The method of claim 1, wherein dimerization is measured in vitro or in situ.

* * * * *